United States Patent
Nagel et al.

(10) Patent No.: US 8,993,602 B2
(45) Date of Patent: Mar. 31, 2015

(54) BENZOIC ACID SALT OF OTAMIXABAN

(75) Inventors: Norbert Nagel, Frankfurt am Main (DE); Bruno Baumgartner, Frankfurt am Main (DE); Harald Berchtold, Frankfurt am Main (DE); Timothy Ayers, Bridgewater, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/008,332

(22) PCT Filed: Mar. 27, 2012

(86) PCT No.: PCT/EP2012/055364
§ 371 (c)(1),
(2), (4) Date: Sep. 27, 2013

(87) PCT Pub. No.: WO2012/130821
PCT Pub. Date: Oct. 4, 2012

(65) Prior Publication Data
US 2014/0024684 A1    Jan. 23, 2014

Related U.S. Application Data

(60) Provisional application No. 61/500,342, filed on Jun. 23, 2011.

(30) Foreign Application Priority Data

Mar. 29, 2011   (EP) .................................. 11305348

(51) Int. Cl.
*C07D 213/89* (2006.01)
*A61K 31/44* (2006.01)
*C07D 213/16* (2006.01)

(52) U.S. Cl.
CPC .............. *C07D 213/89* (2013.01); *A61K 31/44* (2013.01); *C07D 213/16* (2013.01)
USPC .......................................... 514/357; 546/332

(58) Field of Classification Search
None
See application file for complete search history.

(56) References Cited

U.S. PATENT DOCUMENTS 6,080,767 A * 6/2000 Klein et al. ................... 514/357
7,034,160 B2 * 4/2006 Woodward et al. ........... 546/332

FOREIGN PATENT DOCUMENTS

WO    WO 97/24118 A1    7/1997

OTHER PUBLICATIONS

Berge et al., Pharmaceutical Salts, 66(1) J. Pharma. Sci. 1-19 (1977).*
International Search report dated May 4, 2012 issued in PCT/EP2012/055364.
Cohen, M. et al., Randomized, Double-Blind, Dose-Ranging STudy of Otamixaban, a Novel, Parenteral, Short-Acting Direct Factor Xa Inhibitor, in Percutaneous Coronary Intervention, Circulation, (May 22, 2007), vol. 115, pp. 2642-2651.
Guertin, K. R. et al., The Discovery of the Factor Xa Inhibitor Otamixaban: From Lead Identification to Clinical Development, Current Medicinal Chemistry, (2007), vol. 14, No. 23, pp. 2471-2481.
Hinder, M. et al., Direct and rapid inhibition of factor Xa by otamixaban: A pharmacokinetic and pharmacodynamic investigation in patients with coronary artery disease, Clinical Pharmacology and Therapeutics, (Dec. 2006), vol. 80, No. 6, pp. 691-702.

* cited by examiner

*Primary Examiner* — Timothy R Rozof
(74) *Attorney, Agent, or Firm* — Scully, Scott, Murphy & Presser P.C.

(57) ABSTRACT

The invention relates to a benzoic acid salt of methyl(2R,3R)-2-{3-[amino(imino)methyl]benzyl}-3-{[4-(1-oxidopyridin-4-yl)benzoyl]amino}butanoate, and to a benzoic acid salt of methyl(2R,3R)-2-{3-[amino(imino)methyl]benzyl}-3-{[4-(1-oxidopyridin-4-yl)benzoyl]amino}butanoate which is in a crystalline form or in at least partially crystalline form, as well as a process for the preparation of the same, methods of using such salt to treat subjects suffering from conditions which can be ameliorated by the administration of an inhibitor of Factor Xa.

8 Claims, 1 Drawing Sheet

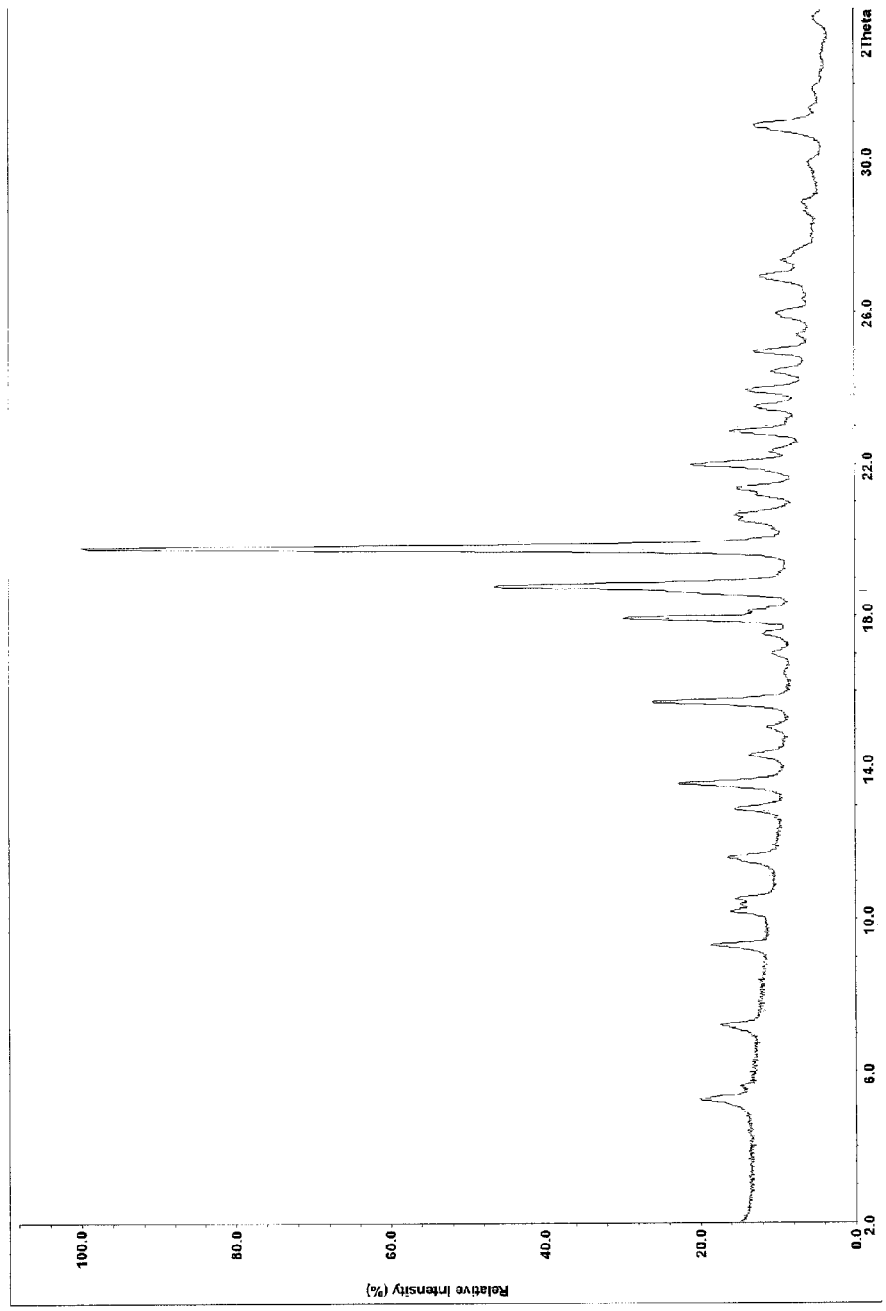

BENZOIC ACID SALT OF OTAMIXABAN

CROSS-REFERENCE TO RELATED APPLICATIONS

This application claims the benefit of U.S. Provisional Application No. 61/500,342 filed on Jun. 23, 2011, the entire contents of which are incorporated herein by reference.

FIELD OF THE INVENTION

The present invention relates to a benzoic acid salt of methyl(2R,3R)-2-{3-[amino(imino)methyl]benzyl}-3-{[4-(1-oxidopyridin-4-yl)benzoyl]amino}butanoate, and to a benzoic acid salt of methyl(2R,3R)-2-{3-[amino(imino)methyl]benzyl}-3-{[4-(1-oxidopyridin-4-yl)benzoyl]amino}butanoate which is in a crystalline form or in at least partially crystalline form, as well as a process for the preparation of the same, methods of using such salt to treat subjects suffering from conditions which can be ameliorated by the administration of an inhibitor of Factor Xa and shows the structure illustrated in Formula I:

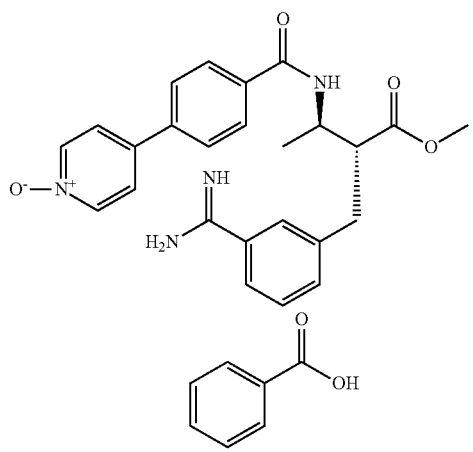

Formula I

BACKGROUND OF THE INVENTION

Methyl(2R,3R)-2-{3-[amino(imino)methyl]benzyl}-3-{[4-(1-oxidopyridin-4-yl)benzoyl]amino}butanoate, (CAS number 193153-04-7) has the International Nonproprietary Name Otamixaban and shows the structure illustrated in Formula II:

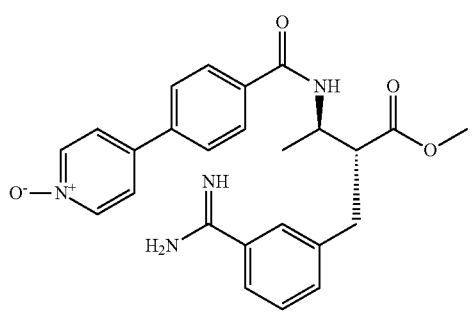

Formula II

Methyl(2R,3R)-2-{3-[amino(imino)methyl]benzyl}-3-{[4-(1-oxidopyridin-4-yl)benzoyl]amino}butanoate use in the preparation of a medicament for treating a patient suffering from, or subject to, conditions which can be ameliorated by the administration of an inhibitor of Factor Xa has been disclosed in WO97/24118.

Factor Xa is the penultimate enzyme in the coagulation cascade. Factor Xa (fXa) is a critical serine protease situated at the confluence of the intrinsic and extrinsic pathways of the blood coagulation cascade. FXa catalyses the conversion of prothrombin to thrombin via the prothrombinase complex. Its singular role in thrombin generation, coupled with its potentiating effects on clot formation render it an attractive target for therapeutic intervention.

Both free factor Xa and factor Xa assembled in the prothrombinase complex (Factor Xa, Factor Va, calcium and phospholipid) are inhibited by Otamixaban. Factor Xa inhibition is obtained by direct complex formation between the inhibitor and the enzyme and is therefore independent of the plasma co-factor antithrombin III. Effective factor Xa inhibition is achieved by administering the compound either by continuous intravenous infusion, bolus intravenous administration or any other parenteral route such that it achieves the desired effect of preventing the factor Xa induced formation of thrombin from prothrombin. In vivo experiments have demonstrated that Otamixaban is highly efficacious in rodent, canine and porcine models of thrombosis. In addition, recent clinical findings indicate that Otamixaban is efficacious, safe and well tolerated in humans and therefore has considerable potential for the treatment of acute coronary syndrome (K. R. Guertin and Yong-Mi Choi; 2007; Current Medicinal Chemistry, Vol. 14, No. 23; p. 2471-2481). Clinical findings in a dose-ranging clinical trial indicate that Otamixaban reduced prothrombin fragments 1+2 significantly more than unfractionated heparin at the highest dose regimen (Cohen et al., Circulation, Vol. 115, No. 20, May 2007, pages 2642-2651), but said clinical findings do not show data in comparison of age or renal impairment. Further clinical trials demonstrated that Otamixaban induces dose-dependent, rapid direct factor Xa inhibition in patients with stable coronary artery disease who are taking their usual comedication, some of whom have mild renal impairment (Hinder et al., Clinical Pharmacology and Therapeutics, Vol. 80, No. 6, 2006, pages 691-702).

A crystalline form of methyl(2R,3R)-2-{3-[amino(imino) methyl]benzyl}-3-{[4-(1-oxidopyridin-4-yl)benzoyl] amino}butanoate hydrochloride, 2-butanol hemisolvate is disclosed in U.S. Pat. No. 7,034,160. The crystalline form of (methyl(2R,3R)-2-{3-[amino(imino)methyl]benzyl}-3-{[4-(1-oxidopyridin-4-yl)benzoyl]amino}butanoate hydrochloride, 2-butanol hemisolvate contains 2-butanol as a solvate which is not favourable for use in solid pharmaceutical compositions and is a hygroscopic compound.

Hygroscopicity is the ability of a substance to attract and hold water molecules from the surrounding environment through either absorption or adsorption with the adsorbing or absorbing material becoming physically 'changed,' somewhat, increase in volume, stickiness, or other physical characteristic changes of the material as water molecules become 'suspended' between the material's molecules in the process. Therefore hygroscopic compounds are generally very unfavorable for use in solid pharmaceutical compositions.

It is an object of the present invention to find a salt of methyl(2R,3R)-2-{3-[amino(imino)methyl]benzyl}-3-{[4-(1-oxidopyridin-4-yl)benzoyl]amino}butanoate with reduced absorption or adsorption of water molecules from the surrounding environment. It has been found that a benzoic acid salt of methyl(2R,3R)-2-{3-[amino(imino)methyl]benzyl}-3-{[4-(1-oxidopyridin-4-yl)benzoyl]amino}butanoate has favorable reduced absorption or adsorption of water molecules from the surrounding environment.

SUMMARY OF THE PRESENT INVENTION

In one embodiment the present invention relates to a benzoic acid salt of methyl(2R,3R)-2-{3-[amino(imino)methyl]benzyl}-3-{[4-(1-oxidopyridin-4-yl)benzoyl]amino}butanoate and shows the structure illustrated in Formula I:

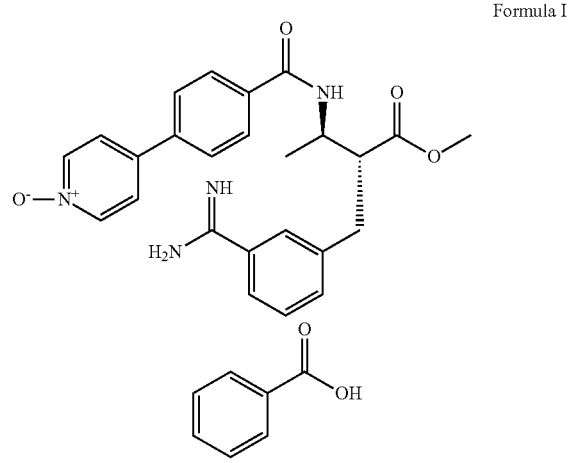

Formula I

In another embodiment the invention relates to a benzoic acid salt of methyl(2R,3R)-2-{3-[amino(imino)methyl]benzyl}-3-{[4-(1-oxidopyridin-4-yl)benzoyl]amino}butanoate, which is in a crystalline form or in at least partially crystalline form.

DETAILED DESCRIPTION OF THE INVENTION

In one embodiment the present invention relates to a benzoic acid salt of methyl(2R,3R)-2-{3-[amino(imino)methyl]benzyl}-3-{[4-(1-oxidopyridin-4-yl)benzoyl]amino}butanoate and shows the structure illustrated in Formula I.

In another embodiment the invention relates to a benzoic acid salt of methyl(2R,3R)-2-{3-[amino(imino)methyl]benzyl}-3-{[4-(1-oxidopyridin-4-yl)benzoyl]amino}butanoate, which is in a crystalline form or in at least partially crystalline form.

Polymorphism is the ability of a single compound to exist in more than one form or crystal structure. Different polymorphs represent distinct solids sharing the same molecular formula, yet each polymorph may have distinct physical properties. A single compound may give rise to a variety of polymorphic forms wherein each form may have different and distinct physical properties, such as different solubility profiles, different thermodynamic stability, different crystallization behavior, different filterability, different melting point temperatures and/or different X-ray diffraction peaks. The difference in the physical properties of different polymorphic forms results from different orientation and intermolecular interactions of adjacent molecules in the solid. Polymorphic forms of a compound can be distinguished by X-ray diffraction and by other methods such as, infrared spectroscopy or Raman spectroscopy.

"Amorphous" means a solid that exhibits in an X-ray powder diffraction pattern measured in transmission with CuKα$_1$ radiation at room temperature no characteristic reflections at degrees 2 theta which can be separated from each other by their diffraction angle oder specific degree 2 theta.

In another embodiment the invention relates to a crystalline benzoic acid salt of Formula I wherein the crystalline salt exhibits in an X-ray powder diffraction pattern measured in transmission with CuKα$_1$ radiation at room temperature a characteristic reflection at degrees 2 theta of 19.8, 18.8 and 17.9, each time±0.2 degrees 2 theta.

In another embodiment the invention relates to a crystalline benzoic acid salt of Formula I wherein the crystalline salt exhibits in an X-ray powder diffraction pattern measured in transmission with CuKα$_1$ radiation at room temperature a characteristic reflection at degrees 2 theta of 22.0, 19.8, 18.8, 17.9, 15.7 and 13.6 each time±0.2 degrees 2 theta.

The selection of characteristic reflections was determined by the number of reflections at a specified degree 2 theta.

In another embodiment the crystalline benzoic acid salt of Formula I may also be characterized by its X-ray powder diffraction pattern substantially by the one shown in FIG. 1, which has been obtained using CuKα$_1$ radiation in transmission mode, wherein the intensities of the reflections depicted in the FIGURE as well as those of the reflections specified above are not a prerequisite, but may vary.

The crystalline benzoic acid salt of formula I may also be characterized by its crystal lattice parameters which have been determined by indexing its powder pattern. The crystalline salt of formula I crystallizes in the orthorhombic crystal system with a=33.524 Å, b=17.928 Å, c=9.896 Å, volume=5947 Å$^3$.

Moreover, crystalline benzoic acid salt of Formula I may also be characterized by its dynamic vapor sorption (DVS) water vapor sorption and desorption isotherms measured at 25° C. Before starting the sorption cycle the crystalline salt of Formula I sample is treated with dry nitrogen gas. As shown in the examples the sorption and desorption isotherms are almost the same wherein a moderate water uptake of 1.1% at 80% room humidity (RH) and 2.0% at 95% RH takes place.

DESCRIPTION OF THE FIGURES

FIG. 1—X-ray powder diffraction pattern of crystalline benzoic acid salt of methyl(2R,3R)-2-{3-[amino(imino)methyl]benzyl}-3-{[4-(1-oxidopyridin-4-yl)benzoyl]amino}butanoate, measured in transmission mode with CuKα$_1$ radiation at room temperature (x-axis: diffraction angle 2theta (2θ) [°]; y-axis: relative intensity The benzoic acid salt of methyl(2R,3R)-2-{3-[amino(imino)methyl]benzyl}-3-{[4-(1-oxidopyridin-4-yl)benzoyl]amino}butanoate may also be prepared by dissolving the methyl(2R,3R)-2-{3-[amino(imino)methyl]benzyl}-3-{[4-(1-oxidopyridin-4-yl)benzoyl]amino}butanoate in aqueous or aqueous-alcohol solution or other suitable solvents to which the benzoic acid or a salt of benzoic acid is added. Under stirring, the mixture can be heated to 65° C. yielding a clear solution and subsequently cooling overnight yields a precipitate. The precipitate obtained can be filtered, washed with water and dried under reduced pressure.

In general, the crystalline benzoic acid salt of methyl(2R, 3R)-2-{3-[amino(imino)methyl]benzyl}-3-{[4-(1-oxidopyridin-4-yl)benzoyl]amino}butanoate of the present invention (in the following benzoic salt of formula I) can be obtained by crystallizing or recrystallizing compound of Formula I, starting from a solution of compound of Formula I or from a suspension of compound of Formula I or from solid compound of Formula I. A solution of compound of Formula I, or a suspension of compound of Formula I, may have been obtained at the end of the chemical synthesis of compound of Formula I, or it may have been obtained by dissolving or suspending previously synthesized crude compound of Formula I. The term "crude compound of Formula I" comprises any form of compound of Formula I, e.g. the material directly obtained from chemical synthesis, a distinct crystalline form or amorphous material of the compound of Formula I.

More specifically, the crystalline salt of Formula I of the invention can be obtained by
(a) providing a solution or suspension of compound of Formula I, for example by dissolving or suspending crude compound Formula I in a suitable solvent such as an alcohol, e.g. methanol, ethanol, 2-propanol; wherein a solution of compound of Formula I generally is a clear solution and may optionally have been filtered,
(b) maintaining, heating, cooling and/or concentrating the solution or suspension and/or adding one or more further solvents, with or without agitation such as stirring, to form crystals of a desired distinct crystalline form or solvate or to allow the formation of a desired distinct crystalline form or solvate, and
(c) isolating the distinct crystalline salt of Formula I.

The processes for preparing crystalline forms and solvates of compound of Formula I can be performed with conventional equipment and according to standard procedures. For example, concentrating of a solution or suspension in step (b) may be done by distilling off solvent partially or totally at atmospheric pressure or at reduced pressure. Isolating of a crystalline form or solvate in step (c) may be done by any conventional technique such as filtration or vacuum filtration or centrifugation. Isolating may also comprise drying, e.g. by applying elevated temperatures and/or reduced pressure, for example at moderately reduced pressure at about room temperature, i.e. a temperature of about 18° C. to about 65° C., for example about 20° C., or at about 65° C.

In a preferred embodiment, the solution or suspension may be seeded in step (a) or step (b) to promote crystallization. Seeding is preferably done with a small amount of the crystalline salt of Formula I already prepared.

The benzoic acid salt of methyl(2R,3R)-2-{3-[amino (imino)methyl]benzyl}-3-{[4-(1-oxidopyridin-4-yl)benzoyl]amino}butanoate of the present invention (in the following benzoic salt of formula I) may be useful in inhibiting Factor Xa. Accordingly, the present invention provides methods for the treatment or prevention of a pathological condition that may be capable of being modulated by inhibiting production of Factor Xa.

Examples of pathological conditions that may be capable of being treated with the benzoic salt of formula I of the present invention include, for example, acute myocardial infarction (AMI), non-ST elevation myocardial infarction, unstable angina, thromboembolism, acute vessel closure associated with thrombolytic therapy, percutaneous transluminal coronary angioplasty (PTCA), transient ischemic attacks, stroke, intermittent claudication, and restenosis.

The benzoic salt of formula I described herein thus may be useful for, inter alia, inhibiting blood coagulation by virtue of their general ability to inhibit the penultimate enzyme in the coagulation cascade, Factor Xa, rather than thrombin. Benzoic salt of formula I within the scope of the present invention may exhibit marked pharmacological activities according to tests described in the literature, including in vivo tests and in vitro tests, the latter of which are believed to correlate to pharmacological activity in humans and other mammals. For example, both free Factor Xa and Factor Xa assembled in the prothrombinase complex (Factor Xa, Factor Va, calcium and phospholipid) may be inhibited. Factor Xa inhibition may be obtained by direct complex formation between the inhibitor and the enzyme and is therefore independent of the plasma co-factor antithrombin III. Effective Factor Xa inhibition may be achieved by administering the benzoic salt of formula I according to the invention by continuous intravenous infusion, bolus intravenous administration or any other suitable route such that it may achieve the desired effect of preventing the Factor Xa induced formation of thrombin from prothrombin.

In addition to their use in anticoagulant therapy, Factor Xa inhibitors may be useful in the treatment or prevention of other diseases in which the generation of thrombin may play a pathologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor. Inhibition of Factor Xa may effectively block thrombin generation and therefore neutralize any pathologic effects of thrombin on various cell types.

The methods preferably comprise administering to a patient a pharmaceutically effective amount of the benzoic salt of formula I of the present invention, preferably in combination with one or more pharmaceutically acceptable carriers or excipients. The relative proportions of pharmaceutical compositions and carrier and/or excipient may be determined, for example, by the solubility and chemical nature of the materials, chosen route of administration and standard pharmaceutical practice.

The dosage of the benzoic salt of formula I that will be most suitable for prophylaxis or treatment may vary with the form of administration, the particular novel form of the compound chosen and the physiological characteristics of the particular patient under treatment. Broadly, small dosages may be used initially and, if necessary, increased by small increments until the desired effect under the circumstances is reached.

Generally speaking, in the adult, suitable doses may range from about 0.01 to about 100 mg/Kg body weight, and all combinations and subcombinations of ranges and specific doses therein. Preferred doses may be from about 0.01 to about 10 mg/kg body weight per day by inhalation, from about 0.01 to about 100, preferably 0.1 to 70, more preferably 0.5 to 10 mg/Kg body weight per day by oral administration, and from about 0.01 to about 50, preferably 0.01 to 10 mg/Kg body weight per day by intravenous administration. In each particular case, the doses may be determined in accordance with the factors distinctive to the subject to be treated, such as age, weight, general state of health and other characteristics which can influence the efficacy of the medicinal product.

The benzoic salt of formula I according to the invention may be administered as frequently as necessary to obtain the desired therapeutic effect. Some patients may respond rapidly to a higher or lower dose and may find much weaker maintenance doses adequate. For other patients, it may be necessary to have long-term treatments at the rate of about 1 to about 4 doses per day, in accordance with the physiological requirements of each particular patient. Generally, the active product may be administered orally about 1 to about 4 times per day. It goes without saying that, for other patients, it may be necessary to prescribe not more than one or two doses per day.

The benzoic salt of formula I of this invention may be administered in oral dosage forms such as tablets, capsules (each of which includes sustained release or timed release formulations), pills, powders, granules, elixirs, tinctures, suspensions, syrups, and emulsions. Solid dosage forms (pharmaceutical compositions) suitable for administration may generally contain from about 1 mg to about 1000 mg of the benzoic salt of formula I per dosage unit.

For oral administration in solid form such as a tablet or capsule, the benzoic salt of formula I can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms may contain a number of additional ingredients referred to herein as "excipients." These excipients include, among others, diluents, binders, lubricants, glidants and disintegrants. Coloring agents may also be incorporated. "Diluents" as used herein, refers to agents which may impart bulk to the formulation to make a tablet a practical size for compression. Examples of diluents are lactose and cellulose. "Binders" as used herein, refers to agents that may be used to impart cohesive qualities to the powered material to help ensure the tablet remains intact after compression, as well as to improve the free-flowing qualities of the powder. Examples of typical binders include lactose, starch and various sugars. "Lubricants", as used herein, have several functions including preventing the adhesion of the tablets to the compression equipment and improving the flow of the granulation prior to compression or encapsulation. Lubricants are in most cases hydrophobic materials. Excessive use of lubricants is undesired, however, as it may can result in a formulation with reduced disintegration and/or delayed dissolution of the drug substance. "Glidants", as used herein, refers to substances which may improve the flow characteristics of the granulation material. Examples of glidants include talc and colloidal silicon dioxide. "Disintegrants", as used herein, refer to substances or mixtures of substances added to a formulation to facilitate the breakup or disintegration of the solid dosage form after administration. Materials that may serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmelose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

As would be apparent to a person of ordinary skill in the art, once armed with the teachings of the present disclosure, when dissolved, crystalline benzoic salt of formula I loses its crystalline structure, and is therefore considered to be a solution of benzoic salt of Formula I. All forms of the present invention, however, may be used for the preparation of liquid formulations in which crystalline benzoic salt of formula I may be, for example, dissolved or suspended. In addition, the crystalline benzoic salt of formula I may be incorporated into solid formulations.

The following non-limiting examples illustrate the inventors' preferred methods for preparing and using the benzoic acid salt of formula I of the present invention.

EXAMPLES

Example 1

Preparation of Compound (III)

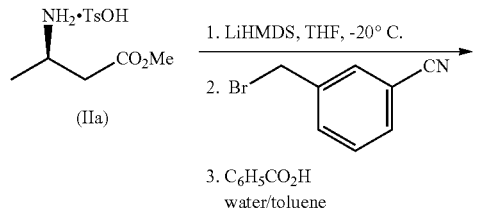

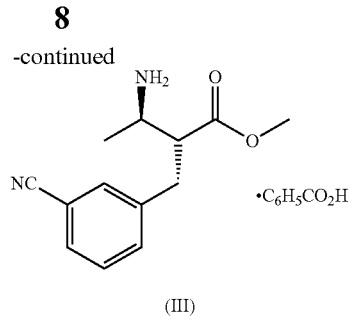

TsOH is p-Toluenesulfonic acid with the formula $CH_3C_6H_4SO_3H$. TsOH refers to the monohydrate. To a reactor were charged Compound (IIa) (100.0 g) and anhydrous tetrahydrofuran (THF) (320 g). The resulting suspension was cooled down to −20±3° C. and lithium hexamethyldisilazide (LiHMDS) (475.6 grams, 1.3 M solution in THF) was added over 55 minutes and stirred for 20 minutes at −20±3° C. A solution of α-bromo-m-tolunitrile in THF (65.1 g in 181 g of THF) was then charged into the reactor over 40 minutes while maintaining the temperature at −20±3° C. and stirred for another 30 minutes. Benzoic acid (126.6 grams) was charged as a solid to the reactor. Water (1000 g) was then added and mixture distilled at a 65±3° C. jacket temperature and 200-233 mbar vacuum. After distilling to a constant pot temperature of 57° C. and constant head temperature of 45° C., the distillation was stopped. Toluene (432 g) was added to the hot solution and stirred while cooling down to 10±2° C. The resulting suspension was then filtered and the filter cake washed with water (250 grams) and toluene (432 grams). Compound (III) was dried at 45-50° C. at ~350 mbar vacuum under a nitrogen stream for 24 hours until constant weight. The isolated solid weighed 76.0 grams (62.0% yield).

Example 2

Preparation of Compound (V)

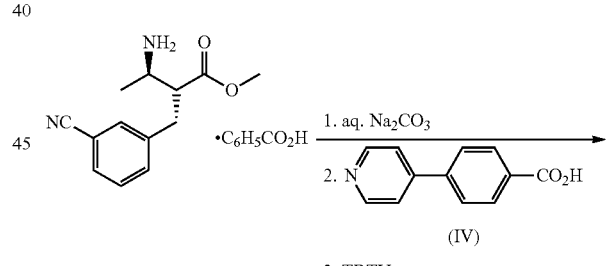

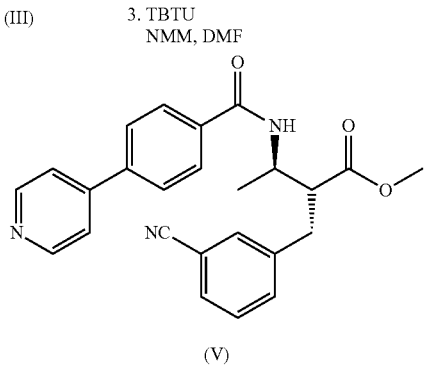

Compound (III) was partitioned between dichloromethane and aqueous sodium carbonate. The organic phase (containing the free base of (III)) was washed with additional aqueous sodium carbonate and was distilled under reduced pressure and solvent exchanged with dimethylformamide (DMF). This solution was assayed for wt/wt content of (III). To a suspension of (IV) (1.0 equivalent vs. (III)) in DMF were added 2 equivalents of 4-methylmorpholine and 1.1 equivalents of O-Benztriazol-1-yl-N,N,N',N'-tetramethyluronium tetrafluoroborate (TBTU). This mixture was stirred at ambient temperature until ester activation was complete (about 90 minutes). The DMF solution of Compound (III) (1 equivalent) was added and the resulting solution stirred overnight after which HPLC indicated that the reaction was complete. Water was added at 75° C. and the mixture was cooled to crystallize the product. The mixture was cooled to 5° C., filtered, and the filter cake was washed with water. The product was dried under reduced pressure at 70° C.

Example 3

Preparation of Compound (VI)

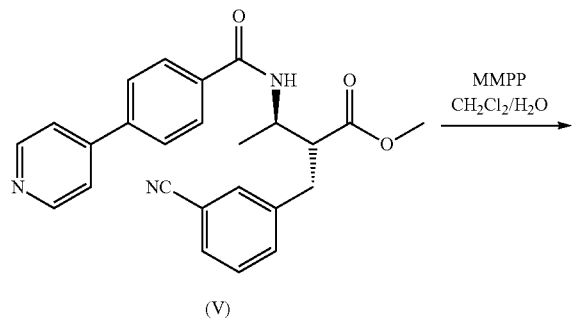

(V)

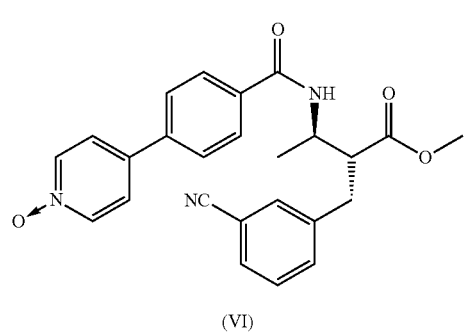

(VI)

In a well-stirred reactor, 45 g of Compound (V) in 450 mL dichloromethane was reacted for at least 5 hours with 61 g of magnesium monoperoxyphthalate (66.4% based on available oxygen, 1.5 eq.) in 450 g of water until the reaction was complete. The phases were separated and the organic phase was washed successively with equal volumes of water, a 5% aqueous sodium bicarbonate solution, and water. The resulting solution was concentrated to an approximately 40 wt % solution and diluted with 180 g of methyl isobutyl ketone (MIBK). Further distillation to remove residual dichloromethane, seeding with appropriate crystals, and cooling gave the product as a crystalline solid. The crystals were filtered, rinsed with 30 g of MIBK, and dried at 50° C. under reduced pressure to give 41.8 g of Compound (VI) (89.3% yield).

Example 4

Preparation of Compound (VII)

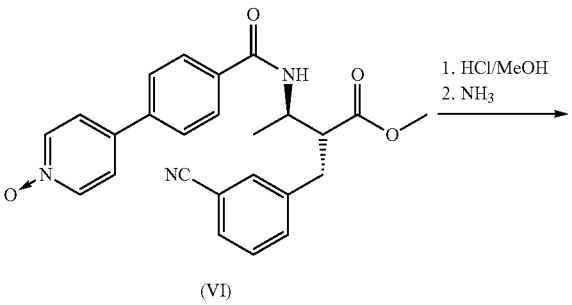

(VI)

(VII)

To a 200-mL jacketed reaction flask were charged Compound (VI) (50.0 g, 116 mmol) and methanol (50 mL). This mixture was cooled to −5° C. and sealed after establishing a partial vacuum (about 100 torr). Anhydrous HCl (52.2 g, 1.43 mol) was added while maintaining the reaction temperature at less than 0° C. The reaction was stirred at 0±1° C. under closed conditions. After 16 hours, the reaction was complete (less than 2 A % (VI) by HPLC). To the intermediate product solution was added anhydrous methanol (100 mL) while maintaining the temperature at less than 5° C. The solution was treated with NH₃ (27.7 g, 1.62 mol) keeping the temperature less than 0° C. Before allowing the mixture to warm to room temperature, a pH check was made of an aliquot dissolved in distilled water (a pH of 8-10 indicates a sufficient charge of ammonia). The reaction was stirred at 20° C. overnight at which point the reaction was complete.

Example 5

Preparation of Compound (VIII) by Solvent Addition

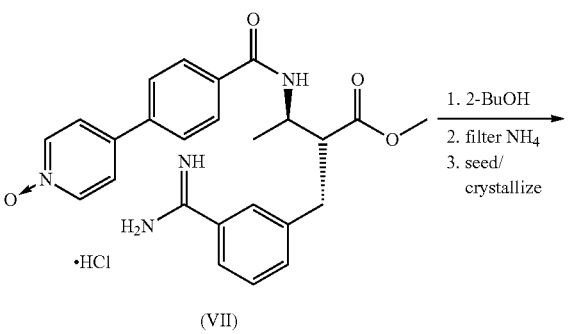

(VII)

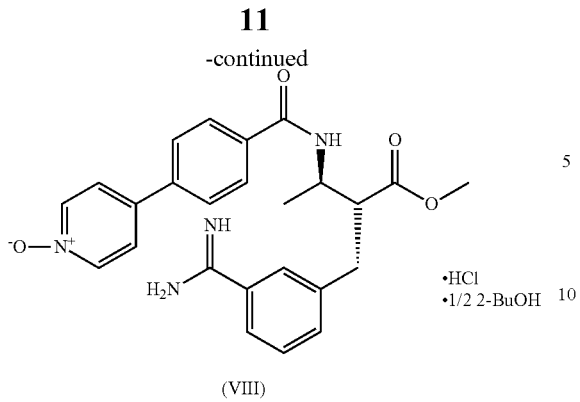

(VIII)

To the ammonium chloride slurry from Example 4 was added 2-butanol (840 mL), and the resulting mixture was stirred for 1 hour while warming to 70° C. The ammonium chloride was removed by hot filtration and the cake was washed with a solution of 20 mL methanol in 160 mL 2-butanol. The filtrates were combined and 0.5 g of seed crystals were added. The mixture was allowed to stir overnight at ambient temperature. The slurry was cooled to −15° C. and held for 2 hours to ensure complete crystallization. The solid was filtered and the reactor and cake were washed with 165 mL of 2-butanol. The solid was dried under reduced pressure at 45° C. to 50 C with a nitrogen bleed giving 44.3 g (73.2%) of Compound (VIII) as an off-white crystalline solid.

Example 6

Preparation of Benzoic Acid Salt

The material was prepared by dissolving 4 g of the compound prepared in Example 5 (the monohydrochloride-hemi-2-butanol-solvate) in 80 ml of hot water and adding 1.11 g of solid sodium benzoate. Under stirring, the mixture was cooled overnight. The precipitate obtained was filtered, washed with water and dried under reduced pressure at 40° C. for 6 hours. The yield amounted to 79.4%.

NMR data confirmed the received salt as a 1:1 ratio of benzoic acid and methyl(2R,3R)-2-{3-[amino(imino)methyl]benzyl}-3-{[4-(1-oxidopyridin-4-yl)benzoyl]amino}butanoate and shows the structure illustrated in the following schema:

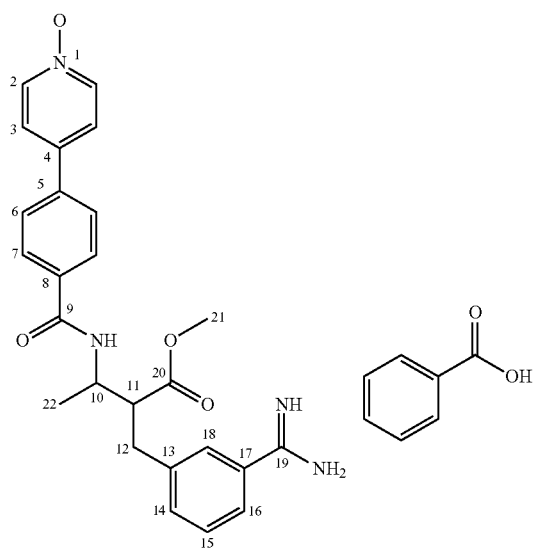

| Calibration | $^1$H | $^{13}$C |
|---|---|---|
| | DMSO = 2.50 ppm | DMSO = 39.476 ppm |

DMSO means dimethyl sulfoxide

For a complete assignment of NMR chemical shifts see Tab. 1.

TABLE 1

NMR chemical shifts of the benzoic acid salt of methyl (2R,3R)-2-{3-[amino(imino) methyl]benzyl}-3-{[4-(1-oxidopyridin-4-yl)benzoyl]amino} butanoate, c = 4.5 mg in 600 μl DMSO at 300° K.

| position | δ ($^{13}$C) [ppm] | m ($^{13}$C) | δ ($^1$H) [ppm] | $^n$J$_{CH}$ correlations |
|---|---|---|---|---|
| 1 | | N | | |
| 2 | 138.95 | | 8.291 | 8.29, 7.86 |
| 3 | 123.86 | | 7.855 | 7.86, 8.29 |
| 4 | 134.34 | C | | 8.29, 7.91 |
| 5 | 138.11 | C | | 7.86, 7.94 |
| 6 | 126.00 | CH | 7.906 | 7.91 |
| 7 | 128.11 | CH | 7.942 | 7.94 |
| 8 | 134.86 | C | | 7.91 |
| 9 | 165.10 | C | | 8.45 7.94 |
| | | NH | | |
| 10 | 46.42 | CH | 4.457 | 3.11 2.98 1.28 |
| 11 | 51.95 | CH | 3.117 | 2.98 1.28 |
| 12 | 33.35 | CH$_2$ | 3.014 2.977 | 7.66 3.11 |
| 13 | 140.45 | C | | 7.50 2.98 |
| 14 | 133.37 | CH | 7.503 | 7.66 7.64 2.98 |
| 15 | 128.91 | CH | 7.508 | |
| 16 | 125.55 | CH | 7.650 | 7.49 7.66 |
| 17 | 129.37 | C | | 7.50 |
| 18 | 127.88 | CH | 7.666 | 2.98 |
| 19 | 166.10 | C | | 7.66 7.64 |
| 20 | 172.90 | C | | 3.52 3.11 2.98 |
| 21 | 51.43 | CH$_3$ | 3.528 | |
| 22 | 17.56 | CH$_3$ | 1.288 | 4.44 3.11 |
| Benz-1 | 171.29 | C | | 7.91 |
| Benz-2 | 138.55 | C | | 7.34 |
| Benz-3 | 128.88 | CH | 7.912 | 7.91, 7.38 |
| Benz-4 | 127.33 | CH | 7.338 | 7.34 |
| Benz-5 | 129.46 | CH | 7.378 | 7.91 |

Alternatively to a solution of 5.0 g of the compound prepared in Example 4 in 100 mL of water was added 2.2 g of sodium benzoate. The mixture was heated on a steam bath until homogeneous. Charcoal (approximately 2 g) was added and this mixture was filtered through Celite® washing with 20 mL of water. Crystallization began immediately. After cooling for 2 h, the solids were collected and washed with water. After drying the solids for 3 days in a vacuum oven at 50° C., 3.9 g (67%) was collected. $^1$H NMR confirmed the salt as a 1:1 ratio of benzoic acid and methyl (2R,3R)-2-{3-[amino(imino)methyl]benzyl}-3-{[4-(1-oxidopyridin-4-yl)benzoyl]amino}butanoate.

Example 7

Differential Scanning Calorimetry (DSC)

The DSC measurement was performed with a Mettler DSC822e (module DSC822e/700/109/414935/0025). 40 μL Aluminum-crucibles with sealed lid and pinhole were used. All measurements were carried out in a nitrogen gas flow of 50 mL/min and a heating rate of 10°/min. The measured data was evaluated via the software STARe V8.10.

The crystalline form used was prepared as in Example 6 and showed during heating from 25° C. to 300° C. an onset peak at 216.01° C. and a peak at 221.15° C.

Example 8

Preparation of a Crystalline Form

A crystalline form was prepared by rapid cooling of a solution of 0.190 g benzoic acid salt of formula I as prepared in Example 6 in 2 mL ethanol from 65° C. to 0° C. Since no precipitation occurred, the sample was left over night at 0° C. The precipitate was isolated by vacuum filtration and then dried under reduced pressure at 25° C.

Alternatively a crystalline form was prepared by controlled cooling of a stirred solution of 0.200 g benzoic acid salt of formula I as prepared in Example 6 in 5.0 mL ethanol from 65° C. to 10° C. in 18 h. The precipitate was isolated by vacuum filtration.

Alternatively, a crystalline form was prepared by controlled cooling of a stirred solution of 0.201 g benzoic acid salt of formula I as prepared in Example 6 in 15 mL 2-propanol and 1.0 mL water from 65° C. to 10° C. in 18 h. Since no precipitation occurred, the solvent was allowed to evaporate at 65° C.

Alternatively, a crystalline form was prepared by dissolving 0.217 g of benzoic acid salt of formula I as prepared in Example 6 in 5.0 mL of ethanol at about 65° C. The solvent was then allowed to evaporate from the stirred solution at the same temperature over night. The solid residue was dried at room temperature under reduced pressure.

Alternatively, a crystalline form was prepared by dissolving 0.197 g of benzoic acid salt of formula I as prepared in Example 6 in 10 mL of 2-propanol and 1.0 mL water at about 65° C. The solvent was then allowed to evaporate from the stirred solution at the same temperature over night. The solid residue was dried at room temperature under reduced pressure.

Example 9

Dynamic Vapor Sorption (DVS)

Moisture sorption/desorption isotherms were recorded on a DVS-1000 from Surface Measurement Systems. Two cycles were run at 25° C., in which the sample was first treated with dry nitrogen gas and then the relative humidity was stepwise increased from 0 to 95% and subsequently decreased again back to 0% and the weight of the sample was measured. Typical total measurement times for both cycles were about 20 to 30 hours.

The measured data for the benzoic acid salt of methyl(2R,3R)-2-{3-[amino(imino)methyl]benzyl}-3-{[4-(1-oxidopyridin-4-yl)benzoyl]amino}butanoate as prepared in Example 8 are shown in the following table 2.

TABLE 2

| DVS Isotherm at 24.9° C. | | | | |
|---|---|---|---|---|
| | Target | Change In Mass (%) | | |
| | RH (%) | Sorption | Desorption | Hysteresis |
| Cycle 1 | 0.0 | 0.000 | −0.035 | |
| | 10.0 | 0.096 | 0.215 | 0.119 |
| | 20.0 | 0.180 | 0.326 | 0.146 |
| | 40.0 | 0.363 | 0.534 | 0.172 |
| | 60.0 | 0.596 | 0.810 | 0.214 |
| | 80.0 | 0.926 | 1.300 | 0.374 |
| | 90.0 | 1.408 | 1.697 | 0.290 |

TABLE 2-continued

| DVS Isotherm at 24.9° C. | | | | |
|---|---|---|---|---|
| | Target | Change In Mass (%) | | |
| | RH (%) | Sorption | Desorption | Hysteresis |
| | 95.0 | 2.031 | 2.031 | |
| Cycle 2 | 0.0 | −0.035 | −0.056 | |
| | 10.0 | 0.109 | 0.198 | 0.089 |
| | 20.0 | 0.226 | 0.310 | 0.084 |
| | 40.0 | 0.461 | 0.523 | 0.062 |
| | 60.0 | 0.742 | 0.800 | 0.058 |
| | 80.0 | 1.241 | 1.299 | 0.058 |
| | 90.0 | 1.616 | 1.687 | 0.071 |
| | 95.0 | 1.999 | 1.999 | |

"RH" means relative humidity; the relative humidity of an air-water mixture is defined as the ratio of the partial pressure of water vapor in the mixture to the saturated vapor pressure of water at a prescribed temperature.
DVS shows a moderate water uptake of 1.1% at 80% RH and 2.0% at 95% RH for the benzoic acid salt of methyl (2R,3R)-2-{3-[amino(imino)methyl]benzyl}-3-{[4-(1-oxidopyridin-4-yl)benzoyl]amino}butanoate.

DVS Comparison Experiment:

Methyl(2R,3R)-2-{3-[amino(imino)methyl]benzyl}-3-{[4-(1-oxidopyridin-4-yl)benzoyl]amino}butanoate monohydrochloride-hemi-2-butanol-solvate as prepared in Example 5.

The measured data for methyl(2R,3R)-2-{3-[amino(imino)methyl]benzyl}-3-{[4-(1-oxidopyridin-4-yl)benzoyl]amino}butanoate monohydrochloride-hemi-2-butanol-solvate as prepared in Example 5 are shown in the following table 3.

TABLE 3

| DVS Isotherm at 25.5° C. | | | | |
|---|---|---|---|---|
| | Target | Change In Mass (%) | | |
| | RH (%) | Sorption | Desorption | Hysteresis |
| Cycle 1 | 0.0 | 0.00 | 0.35 | |
| | 10.0 | 0.79 | 3.33 | 2.54 |
| | 20.0 | 1.28 | 5.29 | 4.01 |
| | 40.0 | 2.22 | 7.14 | 4.91 |
| | 60.0 | 3.69 | 9.78 | 6.09 |
| | 80.0 | 17.79 | 16.92 | −0.87 |
| | 90.0 | 26.66 | 26.07 | −0.59 |
| | 95.0 | 34.13 | 34.13 | |
| Cycle 2 | 0.0 | 0.35 | 0.34 | |
| | 10.0 | 0.69 | 3.17 | 2.48 |
| | 20.0 | 1.32 | 4.97 | 3.65 |
| | 40.0 | 2.67 | 6.78 | 4.11 |
| | 60.0 | 4.57 | 9.41 | 4.84 |
| | 80.0 | 13.43 | 16.37 | 2.94 |
| | 90.0 | 23.91 | 25.32 | 1.41 |
| | 95.0 | 32.86 | 32.86 | |

DVS shows a strong water uptake of 3.69% at 60% RH, 17.79% at 80% RH, 26.66% at 90% RH and 34.13% at 95% RH for methyl (2R,3R)-2-{3-[amino(imino)methyl]benzyl}-3-{[4-(1-oxidopyridin-4-yl)benzoyl]amino}butanoate monohydrochloride-hemi-2-butanol-solvate.

Example 10

Differential Scanning Calorimetry (DSC)

The DSC measurement was performed with a Mettler DSC822e (module DSC822e/700/109/414935/0025). 40 μL Aluminum-crucibles with sealed lid and pinhole were used. All measurements were carried out in a nitrogen gas flow of 50 mL/min and a heating rate of 10°/min. The measured data was evaluated via the software STARe V8.10.

The crystalline form used was prepared as in Example 8 and showed during heating from 25° C. to 300° C. an onset peak at 225.57° C. and a peak at 229.02° C.

Example 11

X-Ray Powder Diffraction (XRPD)

X-ray powder diffraction was performed with Stoe Stadi-P transmission diffractometer using CuK$\alpha_1$ radiation (wavelength is 1.54060 Angström) and a linear position sensitive detectors. Unless stated otherwise, X-ray powder diffraction was performed at room temperature. Samples were investigated in flat preparation. The measured data were evaluated and plotted with the Software WinXPOW V2.12.

The observed X-ray powder diffraction pattern of benzoic acid salt of methyl(2R,3R)-2-{3-[amino(imino)methyl]benzyl}-3-{[4-(1-oxidopyridin-4-yl)benzoyl]amino}butanoate as prepared in Example 8 is displayed in the FIG. 1 (FIG. 1). The X-ray powder diffraction pattern shown in the FIGURE was background-subtracted. The 2θ (2theta) angles in ° (degree) are specified as the number of characteristic reflections. The 2theta angles in degree have the following values in FIG. 1 and the relative intensities are shown in brackets:

5.26 (20), 5.61 (15), 7.20 (17), 9.31 (18), 10.23 (16), 10.40 (15), 10.53 (15), 11.51 (14), 11.62 (16), 12.91 (16), 13.58 (23), 14.33 (14), 15.05 (11), 15.74 (26), 16.51 (9), 17.01 (11), 17.53 (12), 17.93 (30), 18.12 (14), 18.79 (47), 19.80 (100), 20.52 (15), 20.65 (15), 21.20 (13), 21.36 (15), 21.99 (21), 22.32 (11), 22.86 (16), 23.16 (9), 23.51 (13), 23.95 (14), 24.44 (11), 24.96 (13), 25.39 (7), 25.87 (10), 25.97 (10), 26.34 (7), 26.58 (6), 26.94 (12), 27.36 (9), 27.57 (8), 28.67 (6), 28.88 (7), 29.94 (6), 30.91 (13), 31.39 (6), 31.88 (5), 32.25 (4), 32.72 (4), 33.77 (5),

The invention claimed is:

1. Benzoic acid salt of methyl(2R,3R)-2-{3-[amino(imino)methyl]benzyl}-3-{[4-(1-oxidopyridin-4-yl)benzoyl]amino}butanoate.

2. Benzoic acid salt according to claim 1 which is in a crystalline form or in at least partially crystalline form.

3. Benzoic acid salt according to claim 2 wherein the crystalline salt exhibits in an X-ray powder diffraction pattern measured in transmission with CuK$\alpha_1$ radiation at room temperature a characteristic reflection at degrees 2 theta of 19.8, 18.8 and 17.9, each time±0.2 degrees 2 theta.

4. Benzoic acid salt according to claim 2 wherein the crystalline salt exhibits in an X-ray powder diffraction pattern measured in transmission with CuK$\alpha_1$ radiation at room temperature a characteristic reflection at degrees 2 theta of 22.0, 19.8, 18.8, 17.9, 15.7 and 13.6 each time±0.2 degrees 2 theta.

5. Benzoic acid salt according to claim 2, which is characterized by an x-ray powder diffraction pattern substantially in accordance with that shown in FIG. 1.

6. Process for the preparation of the benzoic acid salt according to claim 1, comprising dissolving methyl(2R,3R)-2-{3-[amino(imino)methyl]benzyl}-3-{[4-(1-oxidopyridin-4-yl)benzoyl]amino}butanoate in aqueous or aqueous-alcohol solution and adding benzoic acid or sodium benzoate.

7. A pharmaceutical composition comprising a benzoic acid salt of methyl(2R,3R)-2-{3-[amino(imino)methyl]benzyl}-3-{[4-(1-oxidopyridin-4-yl)benzoyl]amino}butanoate as claimed in claim 1 and a pharmaceutically acceptable carrier or excipient.

8. A method of treating acute myocardial infarction, non-ST elevation myocardial infarction, unstable angina, thromboembolism, acute vessel closure associated with thrombolytic therapy, percutaneous transluminal coronary angioplasty, transient ischemic attacks, stroke, intermittent claudication, and restenosis in a patient in need thereof, comprising administering to said patient a therapeutically effective amount of the pharmaceutical composition of claim 7.

* * * * *